United States Patent [19]

Bradway et al.

[11] Patent Number: 4,699,011
[45] Date of Patent: Oct. 13, 1987

[54] AUTOMATIC COMPACTABILITY TESTER

[75] Inventors: David W. Bradway; Jeffrey G. Danke, both of Neenah, Wis.

[73] Assignee: Hartley Controls Corporation, Neenah, Wis.

[21] Appl. No.: 885,364

[22] Filed: Jul. 14, 1986

[51] Int. Cl.⁴ ............................................. G01N 33/28
[52] U.S. Cl. ........................................ 73/823; 73/818
[58] Field of Search ................ 73/290 R, 298, 823, 73/818, 813

[56] References Cited

U.S. PATENT DOCUMENTS

| 2,373,026 | 4/1945 | Buyer et al. | 73/427 |
| 2,448,964 | 9/1948 | Dietert | 374/55 |
| 2,531,388 | 11/1950 | Black | 73/12 |
| 2,703,492 | 3/1955 | Brissette et al. | 73/818 |
| 2,810,289 | 10/1957 | Button | 73/823 |
| 3,638,478 | 2/1972 | Dietert et al. | 73/823 X |
| 3,998,090 | 12/1976 | Wislocki | 73/823 X |

*Primary Examiner*—Daniel M. Yasich
*Attorney, Agent, or Firm*—Wheeler Law Firm

[57] ABSTRACT

A device for testing the compactibility of a sample of granular material is described including a delivery structure with an invertible riddle, a testing structure with a plunger to compress the sample and an encoder to measure the compactibility of the sample, and a specimen tube mounted on a carriage which traverses between the delivery and testing structures. A wiper levels the sample within the specimen tube. The floor of the specimen tube can be raised to eject the sample after testing and the same wiper cleans the raised floor. A control panel activates and coordinates the operation of the device.

7 Claims, 6 Drawing Figures

AUTOMATIC COMPACTABILITY TESTER

BACKGROUND OF THE INVENTION

The invention relates to granular material testing structure and methods and refers more specifically to automatic structure for determining the compactability of a sample of foundry sand.

A number of devices which compress a sample of sand or soil to test the sample's physical properties are known. See, for example, U.S. Pat. No. 2,810,289 (Button), U.S. Pat. No. 2,703,492 (Brissette, et al), U.S. Pat. No. 2,448,964 (Dietert) and U.S. Pat. No. 2,373,026 (Guyer, et al). None of these, however, are automatic to any significant degree. U.S. Pat. No. 3,638,478 (Dietert, et al) discloses a structure which automatically performs a series of tests on a sample of sand contained in a fixed sample cylinder. The structure disclosed therein is complex and contains no means for emptying and cleaning the various parts thereof.

SUMMARY OF THE INVENTION

The present invention provides a structure for measuring the compactability of a specimen of granular material in an automated series of coordinated events, which include: sifting of the granular material by an agitator through a screen in a riddle, delivery of the granular material of desired coarseness to a specimen tube, inversion of the riddle to empty it of coarser, undesired material, levelling of the granular material in the specimen tube as it traverses to the testing portion of the structure, compression of the granular material to determine its compactability, translation of the linear motion of compression to rotational motion and the recording thereof by an encoder, emptying the specimen tube by elevating the floor thereof, wiping clean the elevated floor of the specimen tube to insure that the tube is empty, re-inverting the riddle, and retracting the floor of the specimen tube as it traverses back to the delivery portion of the structure where it can be re-filled, thereby beginning a new test cycle.

The present invention is a relatively simple structure for determining compactability. The automatic nature of the structure increases efficiency and frees the tester for other functions. The present invention provides means for emptying and cleaning the specimen tube and riddle by making the specimen tube moveable and the riddle invertible.

These and other benefits of the present invention will be shown to one skilled in the art from the following description.

DETAILED DESCRIPTION

Figure 2:
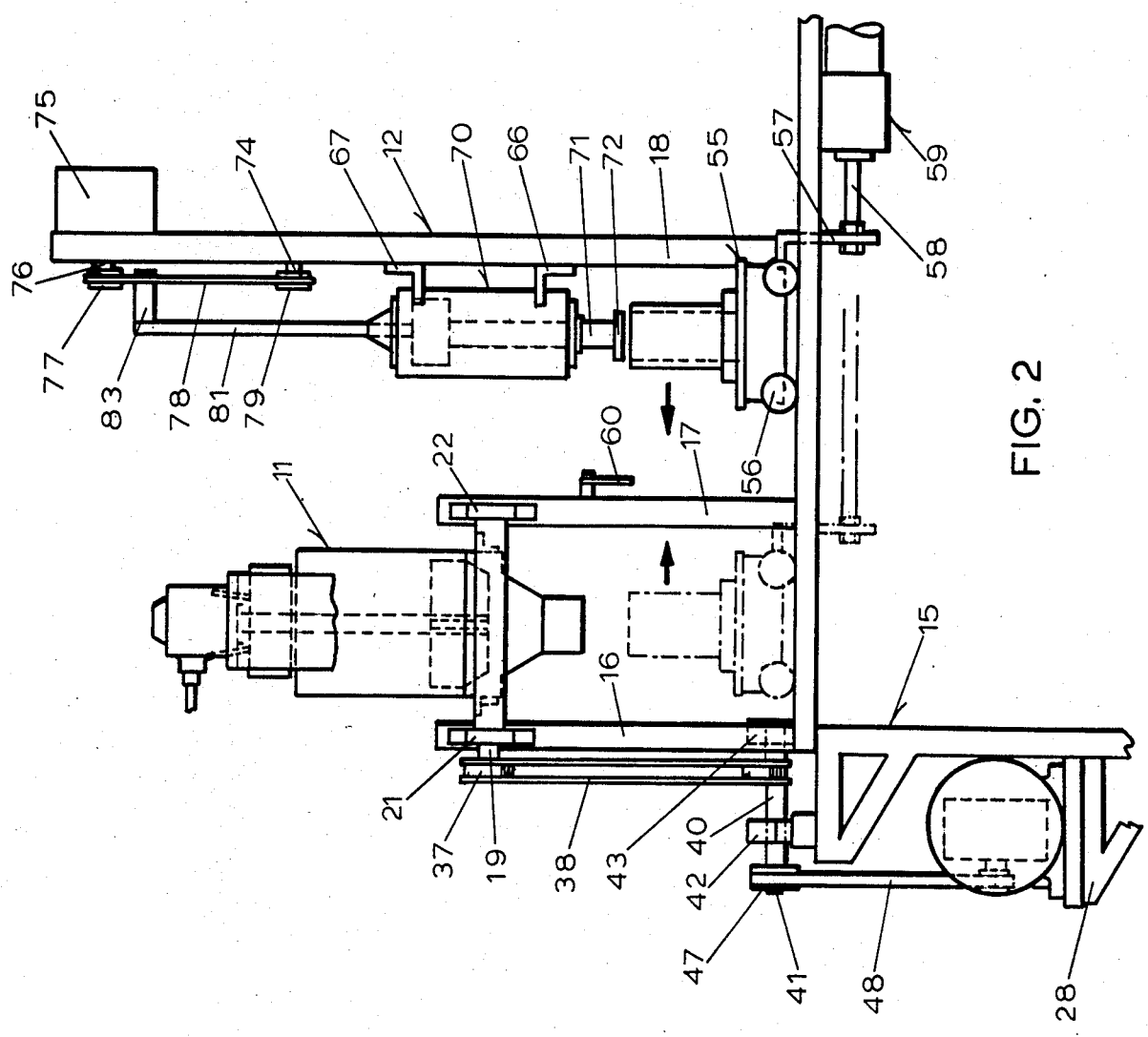
FIG. 2 is a side view of the present invention.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The automatic compactability tester includes a delivery structure 11 and a testing structure 12 both supported by a frame 15. Sand 13 is brought by a conveyor belt system 14 to the delivery structure 11 which is intended to deliver the sand 13 loose and uncompacted to the specimen tube 50.

Figure 1:
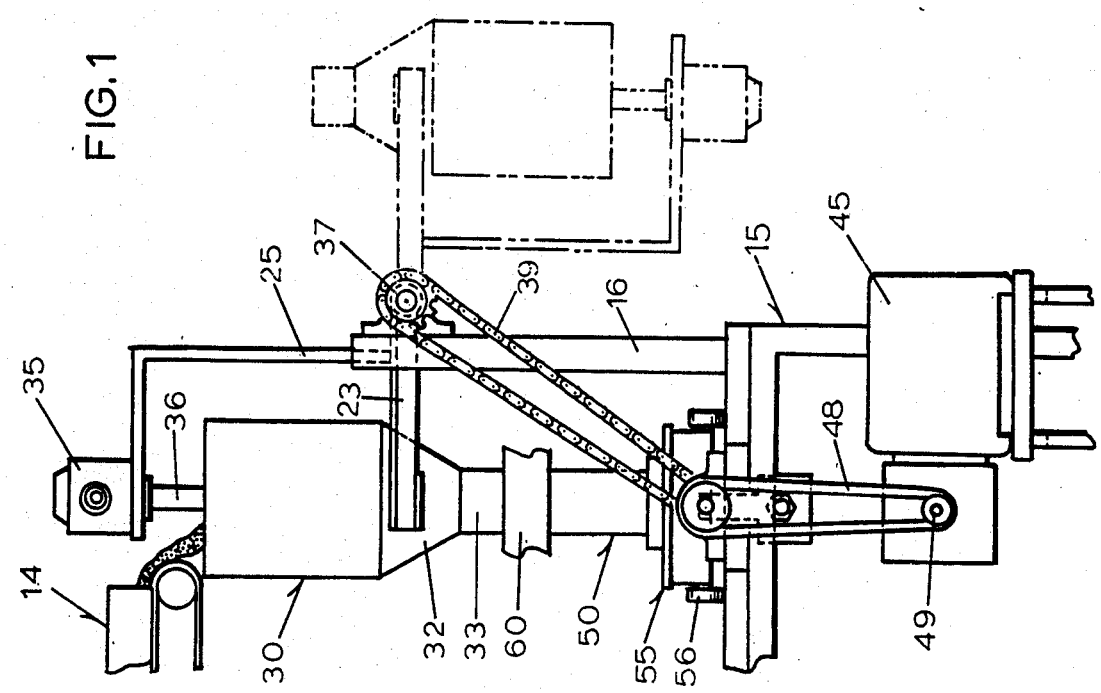
FIG. 1 is an end view of the automatic compactability tester of present invention showing the delivery structure thereof and also schematically showing the riddle in its inverted position.
Figure 3:
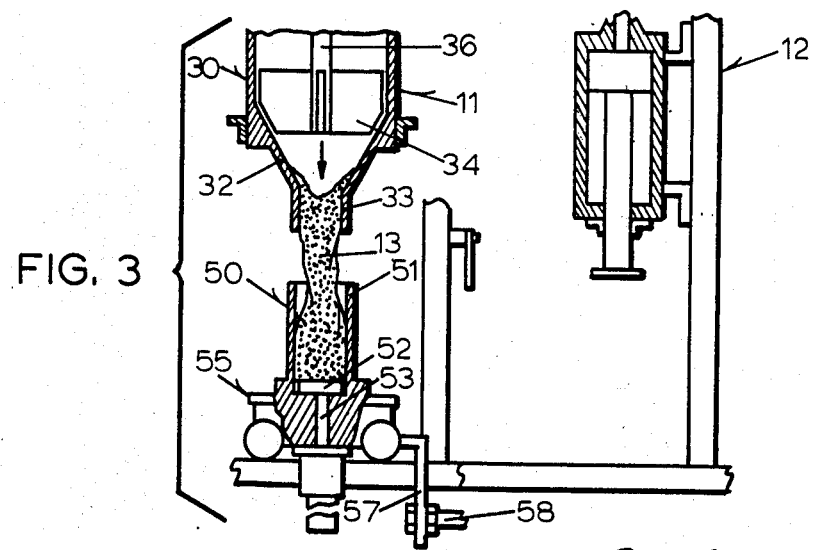
FIG. 3 is a side view of a portion of the present invention with parts cut away showing the carriage located under the delivery structure.

As seen in FIGS. 1 and 2, the delivery structure 11 is primarily supported by vertical supports 16 and 17 which are mounted to the frame 15. Shaft 20 is journalled to bearing blocks 21 and 22 which are mounted on vertical supports 16 and 17, respectively. End 19 of shaft 20 extends beyond bearing block 21 and sprocket 37 is mounted thereon. Horizontal supports 23 and 24 and bracket 25 are mounted on shaft 20. A riddle 30 is mounted between horizontal supports 23 and 24 and the agitator motor 35 is mounted on bracket 25, with agitator shaft 36 extending downward through bracket 25 and into the riddle 30.

Shaft 40 is journalled through bearing block 43 which is mounted on the frame 15 and through bearing block 42 which is mounted on bracket 29 which in turn, is mounted on the frame 15. End 41 of the shaft 40 extends beyond bracket 29 and pulley 47 is mounted thereon. Sprocket 39 is also mounted on shaft 40 and is linked to sprocket 37 by chain 38. Bracket 28 which is mounted on th frame 15 supports motor 45 which turns pulley 49. Pulley 49 is connected to pulley 47 by belt 48.

The delivery structure 11 operates as follows:

A pre-determined amount of sand 13, enough to heapingly fill the specimen tube 50, is brought by the conveyor belt system 14 and cascades into the riddle 30 where it comes to rest on a screen 31 having a desirable mesh located in the generally conical-shaped funnel portion 32 of the riddle 30. The sand 13 is sifted when fins 34 on agitator shaft 36 work the sand 13 through the screen 31. The sand 13 of desired coarseness falls through the cylindrical spout portion 33 of the riddle 30 and into the specimen tube 50 directly below. The specimen tube 50 has a diameter greater than that of the spout portion 33 to insure that no sand 13 is spilled, and is located sufficiently below the riddle 30 to insure that the sand 13 is loose and uncompacted when it falls into the specimen tube 50.

When motor 45 is activated, horizontal supports 23 and 24 rotate 180 degrees around shaft 20, inverting the riddle 30 (see FIG. 1) and emptying it of any remaining sand or gravel which did not pass through screen 31. Airjets (not shown) may be added to aid the removal of such particles. When motor 45 is activated in reverse, the riddle 30 returns to its original position and is ready to deliver another sample.

The specimen tube 50 has cylindrical walls 51 and a plate-like floor 52 which fits slideably within the walls 51. The floor 52 of the specimen tube 50 can be raised or lowered by rods 53 which extends out of and retracts into cylinder 54. The specimen tube 50 is mounted on a carriage 65 and cylinder 54 extends downwardly therefrom.

Figure 4:
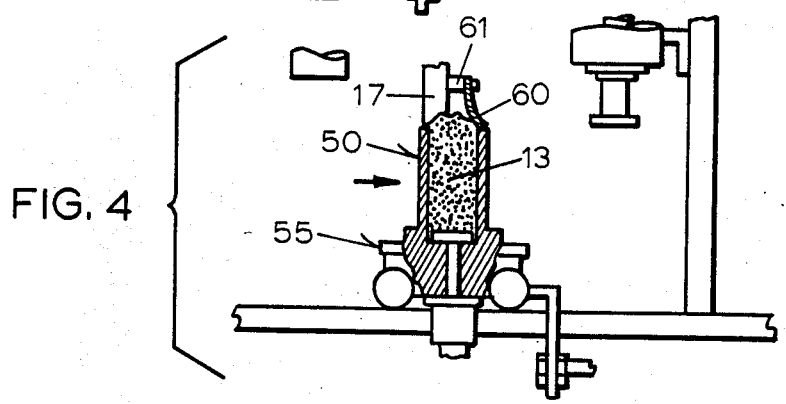
FIG. 4 is a side view of a portion of the present invention with parts cut away showing the operation of the wiper.

Rod 58, which extends out of and retracts into cylinder 59, is fixedly attached to bracket 57 which is mounted on the carriage 55. The wheels 56 of the carriage 55 ride on flat horizontal rails 26 and 27 which are mounted on the frame 15 and separated to accommodate cylinder 54 which extends downwardly from the carriage 55. The carriage 55 and hence the specimen tube 50 can, therefore, traverse from under the riddle 30 on the delivery structure 11 to its correct position on the testing structure 12 and vice versa, as shown in FIG. 1. While in transit, a rubber wiper 60, which is mounted by post 61 to support 17 so as to pass over the top of the specimen tube 50, levels the sand 13 therein (see FIG. 4). Hereinafter the sand 13 in the specimen tube 50 will be referred to as the "specimen" but still, however, denoted by the numeral 13.

The test structure 12 is primarily supported by support 18 which is mounted to the frame 15. An encoder 75 is mounted on support 18 with shaft 76 of the encoder 75 having sprocket 77 mounted thereon. Shaft 74, which is mounted on support 18, has sprocket 79 mounted thereon, and chain 78 joins the two sprockets 77 and 79. The squeeze cylinder 70 is mounted to support 18 by brackets 66 and 67. Rod 71, which extends downwardly out of and retracts into the squeeze cylinder 70, has a plate-like plunger 72 of a size equal to that of the floor 52 of the specimen tube 50. Rod 81, which extends upwardly out of and retracts into squeeze cylinder 70, is connected to chain 78 by bar 83 so that movement of rod 81 causes chain 78 to move, sprockets 77 and 79 and hence shaft 76 to turn, thereby activating the encoder 75.

Figure 5:
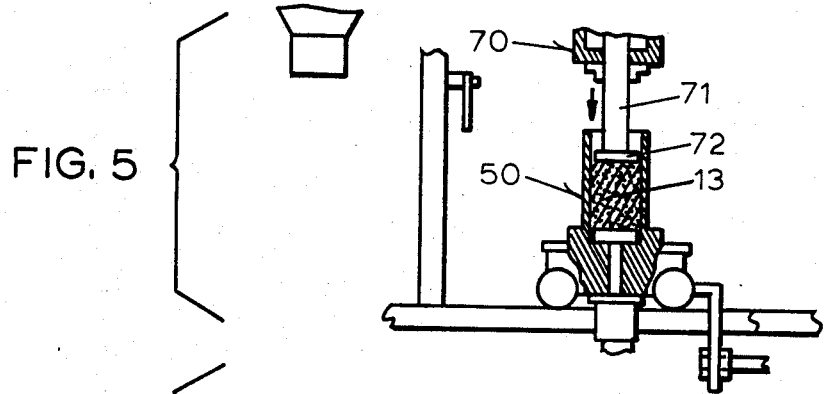
FIG. 5 is a side view of a portion of the present invention with parts cut away showing the carriage under the testing structure and the plunger inserted into the specimen tube.

The test structure 12 operates as follows:

As seen in FIG. 5, when the specimen tube 50 is correctly positioned under the squeeze cylinder 70, rod 71 extends downwardly and plunger 72 uniformly compresses the specimen 13 until a pre-determined pressure is achieved and maintained for a pre-determined length of time. The downward movement of rod 71 results in an equivalent downward movement of rod 81. The downward movement of rod 81 causes an equivalent downward movement of bar 83 and, therefore, chain 78. Sprocket 77 and shaft 76 of the encoder are turned and encoder 75 records this movement. The compactability of the specimen 13 is then simply calculated from the value recorded by the encoder 75.

Figure 6:
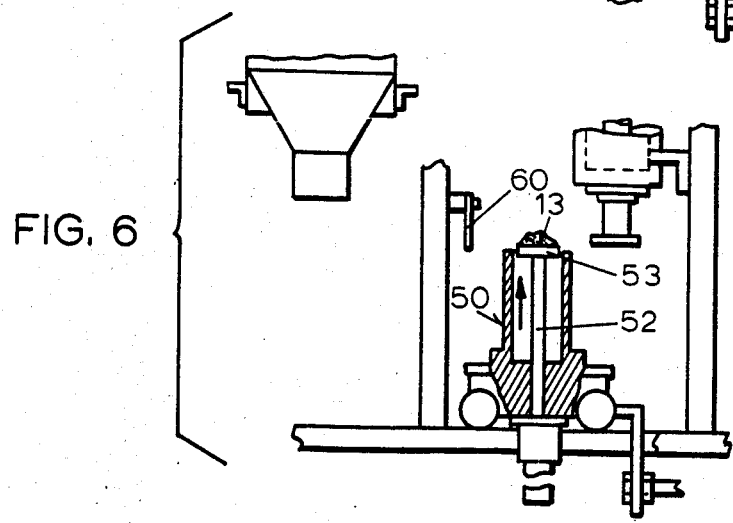
FIG. 6 is a side view of a portion of the present invention with parts cut away showing the bottom of the specimen tube in its raised position.

Once the measurement is taken, rod 71 retracts into the squeeze cylinder 70 thereby withdrawing the plunger 72 from the specimen tube 50. The specimen tube 50 then begins to move toward the delivery structure 11. Before reaching the wiper 60, rod 53 elevates the floor 52 of the specimen tube 50 slightly above the top of the specimen tube 50 as shown in FIG. 6 and rejects the specimen 13. The wiper 60 then sweeps across the floor 52 of the specimen tube 50 to insure that the entire specimen 13 is removed. By the time the specimen tube 50 is once again correctly positioned under the riddle 30, the floor 52 is retracted by rod 51 to the bottom of the specimen tube 50.

A commercially available control panel automatically coordinates the above described actions of the automatic compactability tester. The control panel, conveyor belt system and encoder form no part of the present invention and are, therefore, not disclosed in detail herein. They are, however, within the skill of the art to provide in conjunction with the disclosed automatic compactability testing structure 10.

What is claimed is:

1. A sand compactability testing device for testing the compactability of a sample of granular material having mounting means on which is mounted a delivery structure and a testing structure comprising:

a riddle mounted on said delivery structure; said riddle including a screen positioned to sift granular material;

a specimen tube having a first position below said riddle to receive sifted granular material; said tube having a vertically movable bottom;

means for raising and lowering said bottom of said specimen tube to eject granular material from said tube;

means for levelling granular material within said specimen tube;

means for traversing said specimen tube to a second position at said testing structure;

said testing structure including a compacting plunger and means for moving said plunger in and out of said specimen tube only while mounted on said testing structure in said second position such that granular material within said specimen tube can be uniformly compressed by said plunger;

means for measuring and recording the movement achieved by said plunger in compressing the freely sifted granular material in said tube whereby to determine its compressibility.

2. The device of claim 1 further comprising means for inverting said riddle whereby any granular material which did not pass through said screen is emptied out of said riddle.

3. The device of claim 2 further comprising a control panel to output signals causing a sequence of occurrences including the activation of said traversing means to move said tube from said delivery structure to said testing structure, said moving means to insert said plunger into said tube, said measuring and recording means, said moving means to remove said plunger from said tube, said raising means to raise said bottom of said tube, said traversing means to move said tube from said testing structure to said delivery structure, and said lowering means to lower said bottom of said tube.

4. The device of claim 2 further comprising airjets mounted within said riddle aimed to aid in removing granular maferial which did not pass through said screen from said riddle.

5. The device of claim 1 wherein said levelling means includes a wiper which is mounted such that when said specimen tube traverses from said delivery structure to said testing structure said wiper passes over the top of said specimen tube and when said specimen tube traverses from said testing structure to said delivery structure said wiper sweeps across said bottom of said specimen tube when said bottom is raised.

6. The device of claim 1 wherein said traversing means includes a movable carriage, a piston and cylinder structure, and means for actuating said piston and cylinder structure.

7. The device of claim 1 wherein said measuring means includes a rod which moves in unison with said plunger; an encoder having a shaft; a number of sprockets one of which is mounted on said shaft of said encoder; a chain connecting said sprockets; means for connecting said chain to said rod such that the movement of said rod is reflected by a corresponding movement of said chain.

* * * * *